United States Patent [19]

Nitta et al.

[11] 4,210,894
[45] Jul. 1, 1980

[54] TERMINAL UNIT FOR ELECTRICAL CIRCUIT ELEMENTS AND SENSING DEVICE EMPLOYING SAID TERMINAL UNIT

[75] Inventors: Tsuneharu Nitta, Katano; Ziro Terada, Yao; Shigeru Hayakawa, Hirakata, all of Japan

[73] Assignee: Matsushita Electric Industrial Co., Ltd., Kadoma, Japan

[21] Appl. No.: 938,313

[22] Filed: Aug. 29, 1978

[30] Foreign Application Priority Data

Aug. 30, 1977 [JP] Japan ................... 52-104431
Apr. 13, 1978 [JP] Japan ................... 53-43987

[51] Int. Cl.² ............................................. H01L 7/00
[52] U.S. Cl. ..................... 338/35; 174/139; 174/211; 338/322; 338/324; 338/325
[58] Field of Search ............... 338/35, 34, 322, 324, 338/325; 174/211, 140 C, 139, 152 GM; 23/254 E, 230 E; 340/235; 73/73, 336.5; 361/406, 424; 422/88, 98

[56] References Cited

U.S. PATENT DOCUMENTS

| 2,546,854 | 3/1951 | Foster et al. ............... 174/152 GM |
| 2,577,576 | 12/1951 | Glickman et al. ........... 174/152 GM |
| 2,593,034 | 4/1952 | Kafka ........................... 361/424 X |
| 2,806,991 | 9/1957 | White ............................. 338/34 X |
| 3,479,257 | 11/1969 | Shaver ............................. 338/34 X |
| 3,901,067 | 8/1975 | Boardman, Jr. et al. ......... 338/34 X |
| 3,937,980 | 2/1976 | Seidler et al. ................... 361/424 X |
| 3,939,444 | 2/1976 | Hollyday et al. ................ 361/424 X |
| 4,017,820 | 4/1977 | Ross ................................... 338/35 |
| 4,080,564 | 3/1978 | Nitta et al. ....................... 338/35 X |
| 4,114,056 | 9/1978 | Tsunekawa et al. ............. 361/424 X |

Primary Examiner—C. L. Albritton
Attorney, Agent, or Firm—Wenderoth, Lind & Ponack

[57] ABSTRACT

The present invention is an electrical terminal unit adapted for supporting an electrical circuit element, for example, a moisture responsive resistor or the like and a sensing device employing this terminal unit. The terminal unit makes the influence of the reduction in insulation resistance between the terminals due to adhesion of pollutants to the terminal unit negligible by providing a grounded electrically conductive member or electrode member between the conductive terminal leads extending through a base or substrate of the terminal unit for electrically separating these terminal leads.

10 Claims, 11 Drawing Figures

TERMINAL UNIT FOR ELECTRICAL CIRCUIT ELEMENTS AND SENSING DEVICE EMPLOYING SAID TERMINAL UNIT

BACKGROUND OF THE INVENTION

The present invention relates to an electrical terminal unit and more particularly, to an electrical terminal unit specially adapted for supporting electrical circuit elements or impedance elements for sensing light rays, various gases, humidity, temperatures or the like.

More specifically, when pollutants such as dust, dirt, oil, moisture, etc. adhere to a terminal unit supporting electrical circuit elements of high impedance, the electrical resistance on the surfaces of such a terminal unit is reduced allowing leakage current to flow between the electrically conductive terminal leads or lead wires thereof. The reduction of the surface resistance as described above brings about variations in the characteristics of sensing devices employing high impedance electrical circuit elements. In the present invention, the reduction in the insulation resistance between the electrically conductive terminal lead wires due to adhesion of pollutants to the terminal unit is made negligible by providing an electrically conductive member or electrode member between the terminal lead wires extending through a base or substrate of the terminal unit for electrically separating such terminal lead wires, with the electrode member being grounded.

Commonly, electrical circuit elements are surrounded by casings or the like so as to reduce the effects of the external atmosphere during use. Accordingly, various pollutants such as dust, dirt, oil particles, moisture, etc. in the air rarely adhere to the electrical circuit elements, and thus, variations in the characteristics of these electrical circuit elements due to adhesion of pollutants thereto may normally be ignored.

On the contrary, however, there are some electrical circuit elements directly exposed to the outside atmosphere during use. The outstanding types of these elements are various sensing elements, for example, gas sensors including the smoke sensors, and humidity sensors which are used at all times through direct exposure thereof to air or other gases. Most of these sensing elements have high impedances, and not only their inherent sensitivity but also the leakage current between terminal wires embedded in the base of the terminal unit supporting such sensing elements largely affects the detecting sensitivity and life of such sensing elements. More specifically, the surfaces of sensing elements in general as well as the surfaces of the sensing elements for gas and humidity are subject to soiling by dust, dirt, oil, moisture, etc., while the fixed terminal lead wires and base of the terminal unit are simultaneously soiled thereby increasing the leakage current, with consequent significant errors in the detected current.

By way of example, the present state of the art of such sensing elements will be described hereinbelow with reference to a humidity sensing element.

Humidity sensing elements are important as fundamental elements used in various fields, for example, in industrial fields such as chemistry, chemical agents, paper and food articles, in argicultural fields such as soil control and greenhouse cultivation, in medical fields such as sterilization, microbe cultivation and pharmacy, and also in control of appliances such as air conditioners, microwave ovens, electric ovens, etc. The so-called sensing portion of a humidity sensing element is a moisture responsive resistor which is arranged to sensitively respond to humidity through the variations of air resistance due to fluctuations in humidity. As is well known, metallic oxides such as $Fe_2O_3$, $Al_2O_3$, $Cr_2O_3$, $NiO$, $MgCr_2O_4$, etc. are superior in water absorption properties, and the moisture responsive resistor is formed by utilizing such properties. The moisture responsive elements, which are normally exposed not only to water vapor but to an atmosphere containing various other components during use, tend to lose their inherent moisture responsive resistance properties through a variety of complicated physical and chemical processes between these other components and the various materials employed. Upon deterioration of the moisture responsive properties of the moisture responsive resistor as described above, the original humidity characteristics of this moisture responsive resistor may be restored by eliminating almost all of the absorbed components as well as the oil component from the moisture responsive resistor through heating thereof at temperatures, for example, higher than 400° C. Therefore, by providing a heater or heating element for cleaning purposes in the vicinity of the moisture responsive resistor which is energized, for example, at the time of each use for heating the moisture responsive resistor and thus removing the pollutants adhering to the surface thereof through burning the resistor can be repeatedly used semipermanently. Although the problem related to the deterioration of the moisture responsive characteristics of the moisture responsive resistor may be solved by the employment of a heater as described above, it is still impossible to prevent insulation leakage due to adhesion of dust, dirt, oil, etc. at the base and terminal portions of the terminal unit to which the moisture responsive resistor is connected. In other words, although the properties of the moisture responsive resistor may be repeatedly restored in the manner as described above, it is extremely difficult to remove dust, dirt, oil and the like from the base of the terminal unit and the terminal lead wires supporting this resistor through heat cleaning on the like to restore the insulation resistance thereof, due to complications in structure and increase in size of the sensing device.

Referring to FIG. 1 showing one example of the construction of a conventional humidity sensing device, the moisture responsive resistor S is connected, by lead wires Sl to corresponding ends of terminal lead wires ta and tb which are secured to an insulating base or substrate B in a spaced relation from each other, while the other ends of the terminal lead wires ta and tb which extend through the base B are connected to each other through a signal source V and a detecting resistor R. In the arrangement as described above, the moisture responsive resistor S may be cleaned by providing a heating element nearby as stated earlier, but the oil, dust, moisture, etc. adhering between the terminal lead wires ta and tb, and also on the base B can not be readily removed from the constructional point of view.

SUMMARY OF THE INVENTION

Accordingly, an essential object of the present invention is to provide an improved terminal unit for supporting electrical circuit elements which can be continuously used without any necessity for removing pollutants such as oil, dust, dirt, moisture or the like adhering to its base or substrate and its terminal lead wires.

Another important object of the present invention is to provide an improved terminal unit of the above described type which is simple in construction and reliable in function which can be readily manufactured at low cost.

A further object of the present invention is to provide a sensing device employing an improved terminal unit of the above described type for substantially eliminating the disadvantages inherent in the conventional sensing devices of this kind.

In order to accomplish these and other objects, according to one preferred embodiment of the present invention, the improved terminal unit is provided with an electrically conductive member or electrode member for electrically separating the terminal leads or lead wires of its base to which an electrical circuit element, for example, a moisture responsive resistor is secured, so that the moisture responsive resistor can be continuously used as it is without particularly requiring removal of oil, dust, dirt, moisture and the like adhering between the electrically conductive terminal lead wires and on the base during use.

By the arrangement according to the present invention as described above, any adverse effects to the terminal unit caused by a leakage current due to adhesion of pollutants such as oil component, dust and dirt, moisture, salt, etc., can be reduced to minimum simultaneously improving the detecting sensitivity and the life of the electrical circuit elements and the sensing device employing the terminal unit according to the present invention.

BRIEF DESCRIPTION OF THE DRAWINGS

These and other objects and features of the present invention will become apparent from the following description taken in conjunction with the preferred embodiment thereof with reference to the accompanying drawings, in which.

Before the description of the present invention proceeds, note that like parts are designated by like reference numerals throughout the several views of the accompanying drawings.

DETAILED DESCRIPTION OF THE INVENTION

Figure 2:
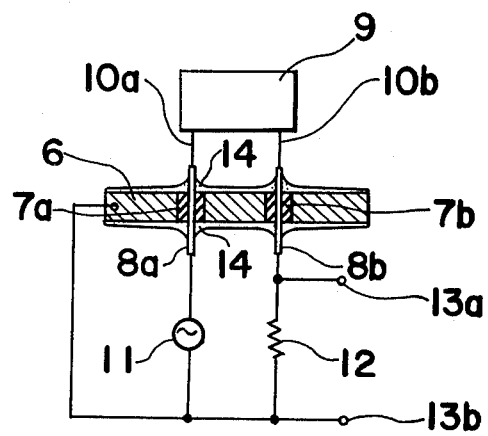
FIG. 2 is a front elevational view, partly in section, showing the structure of a terminal unit according to one preferred embodiment of the present invention having a humidity sensing element attached thereto to form a humidity sensing device.

Referring now to the drawings, there is shown in FIG. 2 a terminal unit according to one preferred embodiment of the present invention to which a moisture responsive resistor 9 is attached to form a humidity sensing device. The terminal unit in FIG. 2 includes a flat plate-like base or substrate 6 made of an electrically conductive material including, for example, Fe, Ni, Al, Cr, etc., a pair of spaced insulating members 7a and 7b of porcelain, glass material or the like, for example, embedded in the base 6 and extending therethrough, and a pair of lead wire securing terminals or terminal lead wires 8a and 8b respectively extending through said insulating members 7a and 7b. Lead wires 10a and 10b of the moisture responsive resistor 9 are connected to corresponding ends of the terminal lead wires 8a and 8b by any suitable means, for example, by soldering. The other end of the terminal lead wire 8a is connected to one end of a signal source 11, and the other end of the terminal lead wire 8b is coupled to one end of a detecting resistor 12. The other ends or ground side terminals of the signal source 11 and detecting resistor 12 are connected to each other. The detecting terminals 13a and 13b are applied to opposite ends of the resistor 12. Finally the base 6 is coupled to terminal 13b. A voltage supply of 60 Hz and one volt, for example, may be employed for the signal source 11. Note here that the terminal lead wires 8a and 8b may be preliminarily secured to the moisture responsive resistor 9. In the above arrangement, pollutants 14 such as oil components, dust and dirt, moisture, etc. gradually adhere between the terminal lead wires 8a and 8b and onto the upper and lower surfaces of the base 6 in the course of time as described earlier.

Figure 3:
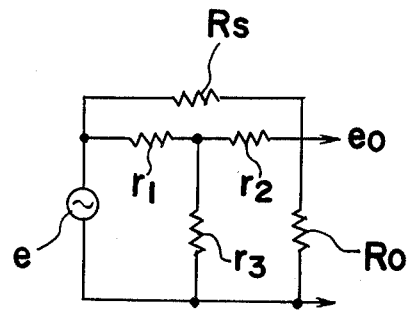
FIG. 3 is an equivalent circuit diagram of the humidity sensing device of FIG. 2.

Referring now to FIG. 3 showing an equivalent circuit of the arrangement of FIG. 2, $R_s$ represents the resistance value of the moisture responsive resistor 9, $r_1$, $r_2$ and $r_3$ the resistance values of the adhering pollutants 14, $R_0$ the resistance value of the detecting resistor 12, e the output of the signal source 11, and $e_0$ the output developed at the terminal 13a. The resistance values of the pollutants 14 adhering between the terminal lead wires 8a and 8b denoted by $r_1$ and $r_2$ are, for example, approximately 5 MΩ each for $r_1$, and $r_2$, although these values may differ depending on the kinds of pollutants 14. The resistance value $r_3$ between the pollutants 14 and the base 6 is, for example, approximately 1 KΩ, since the pollutants 14 are generally thin. The resistance value $R_0$ of the detecting resistor 12 employed is normally approximately 10 KΩ, while the resistance value $R_s$ of the moisture responsive resistor 9 is normally in the vicinity of 10 MΩ. Although the equivalent circuit of FIG. 3 is not completely correct, the assumption as described above creates no particular problems in the evaluation of the circuit construction of FIG. 2. From the above equivalent circuit of FIG. 3, it is seen that the resistance values $r_1$ and $r_2$ are relatively large as compared with $r_3$, and may be represented by the relation as follows.

$$r_1, r_2 \gg r_3 \neq 0$$

The resistance values $r_1$, $r_2$ and $R_s$ are sufficiently large as compared with the resistance value $R_0$ so as to be denoted by the following relation.

$r_1, r_2, R_s >> R_0$

The relation between the output e of the signal source 11 and output $e_0$ developed at the terminal 13a, when calculated employing the equivalent circuit of FIG. 3, is represented by the following equation.

$$e_0 = \frac{\dfrac{R_0 R_2}{R_0 + R_2}}{\dfrac{R_s R_3}{R_s + R_3} + \dfrac{R_0 R_2}{R_0 + R_2}} e$$

where $R_2 = r_2 + r_3 + (r_2 r_3 / r_1)$ $R_3 = r_1 + r_2 + (r_1 r_2 / r_3)$

Upon calculation, the above equation may be given in the form as follows.

$$\frac{e}{e_0} = \frac{R_s(\dfrac{R_0}{r_2} + 1 + \dfrac{r_3}{r_1} + \dfrac{r_3}{r_2})}{R_0(\dfrac{R_s r_3}{r_1 r_2} + 1 + \dfrac{r_3}{r_1} + \dfrac{r_3}{r_2})e} + 1$$

When the relations $r_1, r_2 >> r_3 \neq 0$ and $r_1, r_2, R_s >> R_0$ are taken into consideration here, $(R_0/r_2)$, $(r_3/r_1)$, and $(r_3/r_2)$ are negligible with respect to 1, while $(R_s r_3 / r_1 r_2)$ is also negligible with respect to 1, as seen from consideration of the embodiment ($R_s = 10$ 10 M$\Omega$, $r_1$, $r_2 = 5$ M$\Omega$ and $r_3 = 1$ K$\Omega$) described above.

Therefore, the above equation can be represented as $(e/e_0) = (R_s/R_0) + 1$

Since $(R_s/R_0)$ is sufficiently larger than 1 here, the equation as follows may be obtained by neglecting 1.

$e_0 \approx (R_0/R_s)e$

As is clear from the above equation, the detecting voltage $e_0$ is determined by the resistance values of the detecting resistance 12 and moisture responsive resistor 9, irrespective of the resistance value of the adhering pollutants 14, and thus it becomes unnecessary to remove such pollutants 14.

Figure 1:
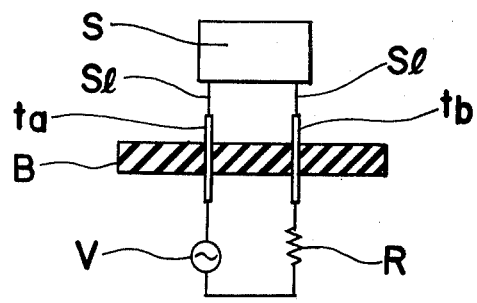
FIG. 1 is a front elevational view, partly in section, showing the structure of a conventional terminal unit referred to above having a humidity sensing element attached thereto to form a humidity sensing device.

The impedance value between the terminal lead wires 8a and 8b, with the moisture responsive resistor 9, signal source 11 and resistance $R_0$ removed, and with the base 6 grounded in the arrangement of the present invention in FIG. 2, and the impedance value between the terminal lead wires ta and tb, with the moisture responsive resistor S, signal source V and resistor R removed in the conventional arrangement of FIG. 1 were measured for various states of adhering pollutants, with the results as tabulated in the table below.

| States of adhering pollutants | Conventional | Present invention |
|---|---|---|
| A | 5.56 × 10$^6$ Ω | 5.88 × 10$^{10}$ Ω |
| B | 3.13 × 10$^6$ Ω | 5.0 × 10$^{10}$ Ω |
| C | 3.08 × 10$^6$ Ω | 6.0 × 10$^{10}$ Ω |
| D | 2.27 × 10$^6$ Ω | 8.0 × 10$^{10}$ Ω |
| E | 2.25 × 10$^6$ Ω | 8.8 × 10$^{10}$ Ω |

As is clear from the above table, as compared with the conventional arrangement, the arrangement of the present invention has a sufficiently large impedance between the terminal lead wires 8a and 8b in spite of the fact that the state of adhesion of the pollutants is the same in both of the arrangements indicating significantly less influence by such adhering pollutants.

Figure 4:
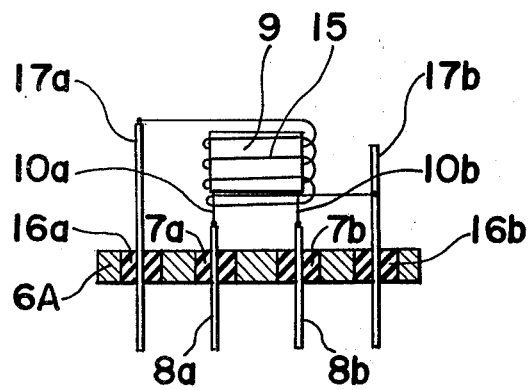
FIG. 4(A) is a view similar to FIG. 2 which particularly shows a modification thereof.
FIG. 4(B) is a top plan view of the sensing device of FIG. 4(A), FIGS. 5 through 7 are views similar to FIG. 2, which particularly show further modifications thereof.
Figure 4:
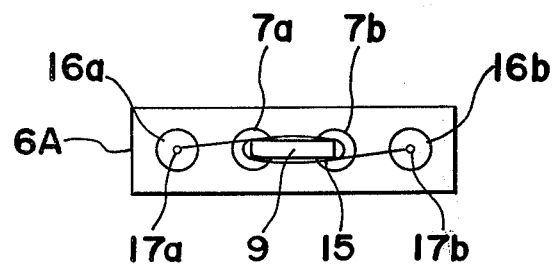

Referring to FIGS. 4(A) and 4(B), there is shown a first modification of the sensing device of FIG. 2. In this modification, a heating wire 15, for example in the form of a coil, is wound around the moisture responsive resistor 9 in a spaced relation to the latter, and the opposite ends of the heating wire 15 are connected to corresponding ends of terminals 17a and 17b extending through insulating members 16a and 16b made of porcelain, glass or the like which are embedded in the base 6A as shown. The other ends of the terminals 17a and 17b are coupled to a suitable power source (not shown) for removing the pollutants (FIG. 2) adhering to the resistor 9 through heating by the wire 15. The heating wire 15 may be a nichrome heating resistor a heating resistor composed of Fe, Ni, Cr, Al, etc.

Figure 5:
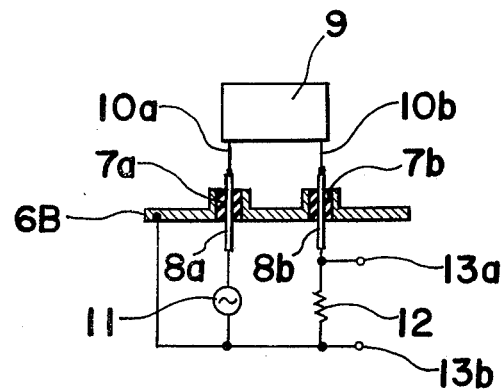

Referring to FIG. 5 showing a second modification of the sensing device of FIG. 2, the base 6 employed in the arrangement of FIG. 2 is replaced by a base 6B of similar electrically conductive material in which the thickness of the conductive portion is reduced on the upper surface thereof except for those portions around the insulating members 7a and 7b through which the terminal lead wires 8a and 8b extend, so as to reduce the cost of the sensing device on the whole. By the modified arrangement of FIG. 5 as described above, the distance between the edge portions of the terminals 8a and 8b on the upper sides is increased, with consequent increase in the resistance values of $r_1$ and $r_2$ for better effects as described earlier. Note that, since the pollutants 14 (FIG. 2) tend to adhere more readily onto the upper surface of the base 6B than to the lower surface thereof, this edge portion distance should preferably be longer on the upper surface.

Figure 6:
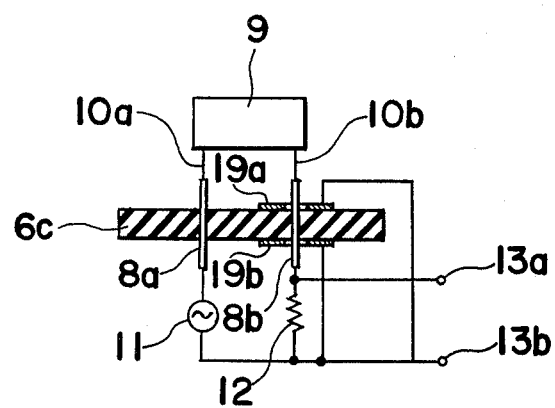

Referring to FIG. 6, there is shown a third modification of the sensing device of FIG. 2. In the modification in FIG. 6, the base 6 formed of electrically conductive material in the embodiment of FIG. 2 is replaced by a base 6C made of electrically insulating material such as oxide porcelain, glass, ethylene tetrafluoride, etc. having the terminal lead wires 8a and 8b extending directly through and secured to the base 6C as shown. Annular electrode plates 19a and 19b made of Ag, Ag-Pd or Pt, for example, are respectively provided on the upper and lower surfaces of the base 6C to surround the terminal lead wire 8b. The electrode plates 19a and 19b are further connected to the ground side of the signal source 11 forming an equivalent circuit similar to that described with reference to FIG. 3. Note that the annular electrode plates 19a and 19b described as surrounding the terminal lead wire 8b in FIG. 6 may be modified to surround the terminal lead wire 8a or to surround both of the terminal lead wires 8a and 8b, or may be further modified to include only the electrode plate 19a disposed on the upper surface of the base 6C, if a covering plate or the like is provided on the lower surface of the base 6C to prevent the adhesion of pollutants.

Figure 7:
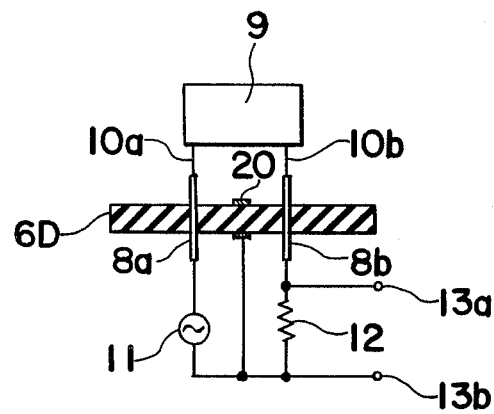

In FIG. 7, showing a fourth modification of the sensing device of FIG. 2, the base 6 of FIG. 2 is replaced by a base 6D of electrically insulating material through which the terminal lead wires 8a and 8b extend and are secured thereat, while a ring-shaped electrode 20 is provided extending around the portion of the base 6D between the terminal lead wires 8a and 8b from the upper surface to the lower surface of base 6D so as to separate the terminal lead wire 8a from the terminal lead wire 8b. The electrode 20 is connected to the ground side of the signal source 11, thus forming an equivalent circuit similar to that in FIG. 3. Note that in cases where the area of the base 6D is sufficiently large, the electrode 20 need not necessarily be a perfect ring shape, but may be cutout in portions thereof. In other words, in the presence of a cutout as described above, there is formed a pathway from the terminal lead wire 8a to 8b along the surface of base 6D not passing through the electrode 20, but if this pathway is long enough, no inconvenience occurs since the pollutants adhering to this pathway have a sufficiently large resistance value. Accordingly, in the above case, the presence of an electrically conductive portion which substantially separates the surfaces of the base 6D between the terminal lead wires 8a and 8b is sufficient for the purpose, and by connecting this conductive portion to the ground side of the signal source 11, the influence of the adhering pollutants can be eliminated.

Figure 8:
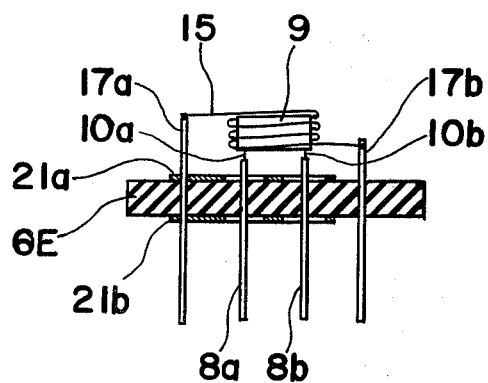
FIG. 8(A) is a view similar to FIG. 4(A) which particularly shows another modification thereof.
FIG. 8(B) is a top plan view of the sensing device of FIG. 8(A)
FIG. 8(C) is a bottom view of the sensing device of FIG. 8(A).
Figure 8:
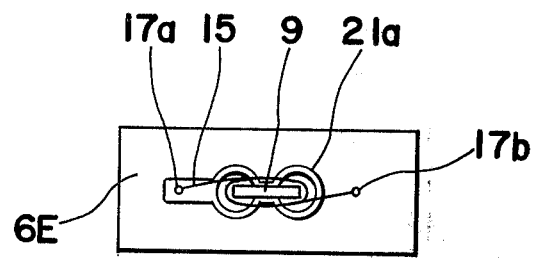
Figure 8:
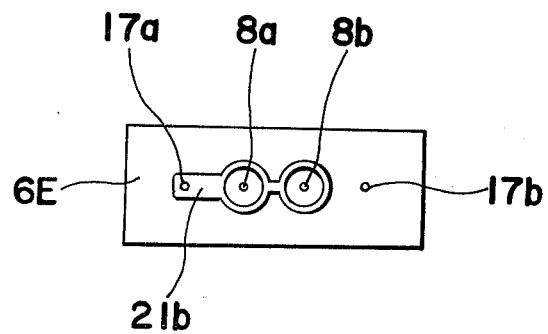

Referring to FIGS. 8(A) through 8(C), there is shown a modification of the sensing device of FIGS. 4(A) and 4(B). In this modification, the base 6A of FIGS. 4(A) and 4(B) is change into to a base 6E of electrically insulating material, through which the terminal lead wires 8a and 8b for the moisture responsive resistor 9 and the terminal wires 17a and 17b for the heating wire 15 extend and are secured thereat. Electrode plates 21a and 21b are respectively provided on the upper and lower surfaces of the base 6E surrounding the terminal lead wires 8a and 8b. The electrode plates 21a and 21b are connected to each other and further connected to the terminal wire 17a for the heating wire 15. The arrangement of FIGS. 8(A) to 8(C) as described above is not only effective for reducing the undesirable influence of the pollutants adhering to the base 6E, but has additional favorable effects as follows. That is to say, since each of the electrode plates 21a and 21b is formed surrounding the terminal lead wires 8a and 8b respectively, the distributed capacitance is reduced, with a consequent improvement in the frequency characteristics. Moreover, owing to the flat annular configuration of the electrode plates 21a and 21b surrounding the terminal lead wires 8a and 8b, the reactance component in the shielding effect has a minimum value, with a consequent uniform electric field distribution and improved voltage breakdown characteristics.

In the foregoing modifications of FIGS. 4(A) through 8(C), the other constructions and functions of the sensing devices are generally similar to those of the sensing device of FIG. 2, and therefore detailed description thereof has been omitted for brevity.

Note that the electrodes 19a, 19b, 20, and 21a and 21b described with reference to the embodiment of FIGS. 6 through 8(C) may be readily formed by the known plane printing technique or deposition at low cost.

Note that glass (silicate of glass, etc. containing alkaline earth), oxide porcelain or metal oxide sintered material (alumina, steatite, silastic and the like), and fluorine-containing resin such as ethylene tetrafluoride, etc. which are not readily subjected to adhesion by oil, dust, dirt, and moisture and which have high electrical insulation, good resistance against salt and also sufficient strength are particularly suitable for actual use for the insulating materials used for the insulating members 7a, 7b, 16a and 16b, and the bases 6C, 6D and 6E in the foregoing embodiments.

As is clear from the foregoing description, according to the present invention, the undesirable influence of leakage current caused by oil components, dust, dirt, moisture, salt, etc. adhering to the surfaces of terminal units supporting various kinds of sensing elements which are exposed to fluids during use are minimized, with remarkable effects such as improvements in the detecting sensitivity, and prolongation of life against aging, etc.

Although the present invention has been fully described by way of example with reference to the accompanying drawings, note that various changes and modifications are apparent to those skilled in the art. Therefore, unless such changes and modifications otherwise depart from the scope of the present invention, they should be construed as included therein.

What is claimed is:

1. An electrical sensing device comprising:
   a grounded electrically conductive substrate having a pair of bores disposed therein;
   a pair of electrically insulating members disposed in respective bores of said electrically conductive substrate;
   a pair of electrically conductive terminal leads extending through respective bores of said electrically conductive substrate, and embedded in and supported by respective electrically insulating members thereby being electrically insulated from said electrically conductive substrate; and
   a sensing element exposed to the atmosphere having a pair of terminals connected to respective terminal leads and having an electrical impedance which varies in response to changes in an atmospheric quantity.

2. An electrical sensing device as claimed in claim 1 wherein said electrically conductive substrate has a pair of additional bores disposed therein, said electrical sensing device further comprising:
   a pair of additional electrically insulating members disposed in respective additional bores of said electrically conductive substrate;
   a pair of electrically conductive heating wire terminal leads extending through respective additional bores of said electrically conductive substrate, and embedded in and supported by respective additional electrically insulating members thereby being electrically insulated from said electrically conductive substrate; and
   a heating wire disposed near said sensing element having opposite ends connected to respective heating wire terminal leads for heating said sensing element when an electrical current is passed therethrough.

3. An electrical sensing device comprising:
   an electrically insulating substrate having a pair of opposite main surfaces;
   a pair of electrically conductive terminal leads embedded in and supported by said electrically insulating substrate, extending through said electrically insulating substrate between said main surfaces thereof;
   a pair of grounded electrode members disposed on respective main surfaces of said electrically insulating substrate having at least a portion thereof between said terminal leads and connected to each other; and a sensing element exposed to the atmosphere having a pair of terminals connected to respective terminal leads and having an electrical impedance which varies in response to changes in an atmospheric quantity.

4. An electrical sensing device as claimed in claim 3, wherein said electrode members are disposed on said electrically insulating substrate so as to surround at least one of said terminal leads.

5. An electrical sensing device as claimed in claim 4, wherein said electrode members are disposed on said electrically insulating substrate so as to surround each of said terminal leads.

6. An electrical sensing device as claimed in claim 3 further comprising:
a pair of electrically conductive heating wire terminal leads embedded in and supported by said electrically insulating substrate, extending through said electrically insulating substrate between said main surfaces thereof, one of said heater terminal leads being connected to said grounded electrode members; and
a heating wire disposed near said sensing element having opposite ends connected to respective heating wire terminal leads for heating said sensing element when an electrical current is passed therethrough.

7. An electrical terminal unit as claimed in claim 3, wherein said electrically insulating substrate is composed of at least one material selected from the group consisting of glass, fluorine-containing resin and metal oxide sintered material.

8. An electrical sensing device comprising:
an electrically insulating substrate having a pair of opposite main surfaces;
first and second electrically conductive terminal leads embedded in and supported by said electrically insulating substrate, extending through said electrically insulating substrate between said main surfaces thereof;
a pair of electrode members disposed on respective main surfaces of said electrically insulating substrate having at least a portion thereof between said terminal leads and connected to each other;
a sensing element exposed to the atmosphere having a pair of terminals connected to respective terminal leads and having an electrical impedance which varies in response to changes in an atmospheric quantity;
an electrical power source having a first terminal connected to said first terminal lead and a second terminal connected to said pair of electrode members; and
a resistor connected between said second terminal lead and said second terminal of said electrical power source.

9. An electrical sensing device as claimed in claim 8, wherein said sensing element is a humidity sensor.

10. An electrical sensing device as claimed in claim 8, further comprising an electrical heating member disposed in the vicinity of said sensing element for heating said sensing element when an electrical current is passed therethrough.

* * * * *